US00PP16741P3

(12) United States Plant Patent
Davidson

(10) Patent No.: US PP16,741 P3
(45) Date of Patent: Jun. 27, 2006

(54) ***MONARDA* PLANT NAMED 'CORAL REEF'**

(50) Latin Name: *Monarda didyma*
Varietal Denomination: Coral Reef

(75) Inventor: Campbell G. Davidson, Morden (CA)

(73) Assignee: Her Majesty the Queen in right of Canada as represented by the Minister of Agriculture, Ottawa (CA)

( * ) Notice: Subject to any disclaimer, the term of this patent is extended or adjusted under 35 U.S.C. 154(b) by 83 days.

(21) Appl. No.: 10/844,339

(22) Filed: May 13, 2004

(65) Prior Publication Data

US 2005/0257304 P1 Nov. 17, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Buchanan Ingersoll PC

(57) ABSTRACT

A new and distinct *Monarda* or Bee-Balm cultivar is provided that displays an upright mounded growth habit and frequently assumes a mature height of approximately three to four feet. Attractive bright coral pink blossoms commonly are formed from June through August. The foliage is dark green, contrasts well with the blossom coloration, and displays a strong minty fragrance. Good resistance to Powdery Mildew is displayed. The plant is well suited for growing as attractive ornamentation in the landscape.

2 Drawing Sheets

Figure 1:
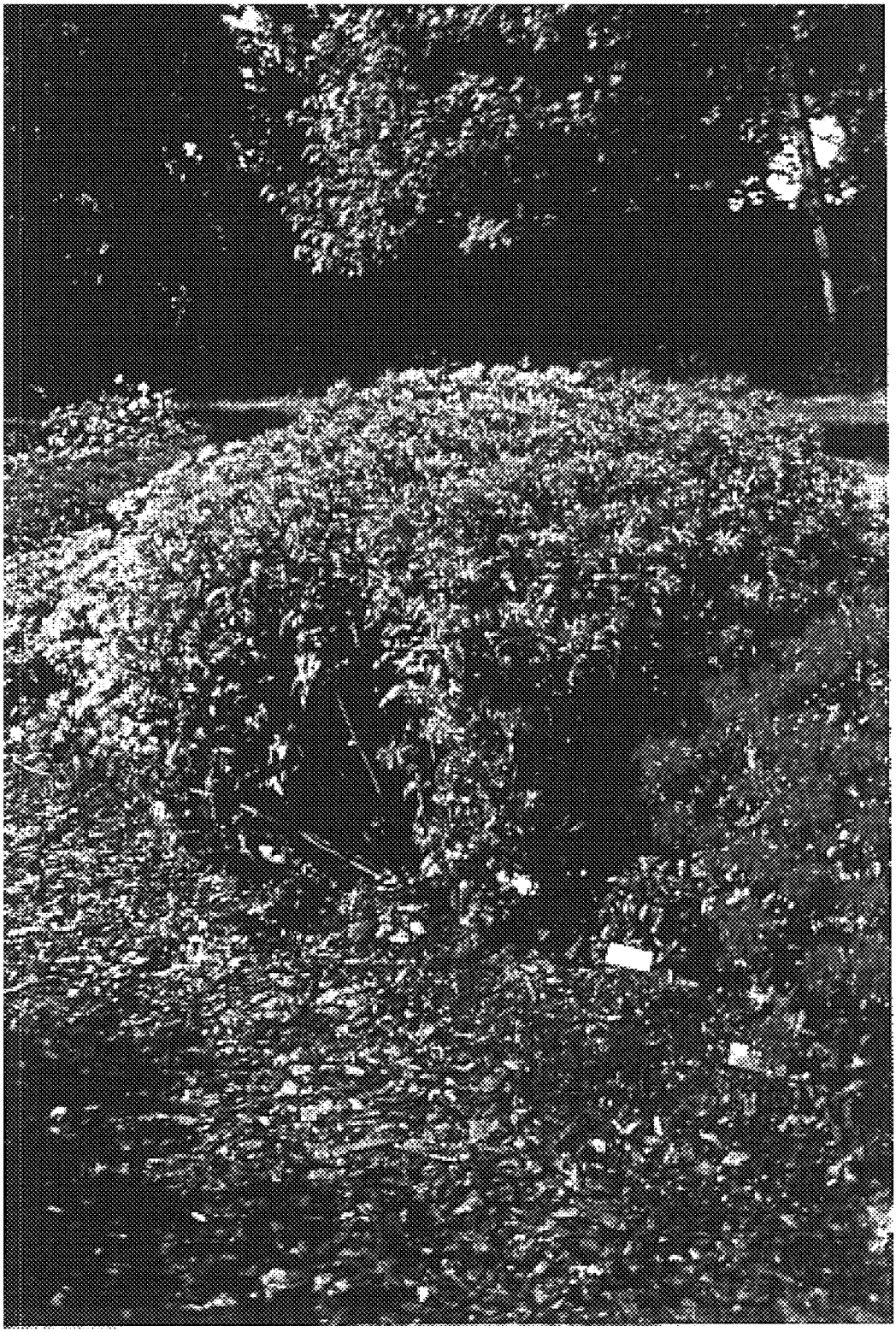

Botanical commercial classification: *Monarda didyma*/ Monarda Plant.
Varietal denomination: cv. 'Coral Reef'.

SUMMARY OF THE INVENTION

The new and distinct *Monarda* (Bee-Balm) cultivar of the present invention was the product of a controlled breeding program carried out at Morden, Manitoba, Canada. The cross that produced the new variety was made in 1990. The female parent was *Monarda didyma 'Mahogany' (non-patented in the United States), and the male parent was Monarda didyma 'Marshall's Delight' (non-patented in the United States. See HortScience*, 24 (3) 525 (1989) where the 'Marshall's Delight' cultivar is discussed. During 1993 a single plant of the new variety was selected and initially was designated No. 9301 and subsequently Baileef. This plant was further studied in the field evaluations during 1994, 1995, 1996, and 1999. It was found that the new *Monarda* plant of the present invention exhibits the following combination of characteristics:

(a) forms attractive bright coral pink blossoms,
(b) forms attractive dark green leaves that display a strong minty fragrance,
(c) displays an upright mounded growth habit and commonly assumes a mature height of approximately three to four feet,
(d) grows well in U.S.D.A. Hardiness Zone Nos. 3 to 8,
(e) displays good resistance to Powdery Mildew, and
(f) is well suited for growing as attractive ornamentation in the landscape.

The bright coral pink blossom coloration contrasts nicely with the dark green foliage coloration, is believed to be unique, and causes the plant to stand out in the landscape. The new plant performs well in full sun and no major insect problems have been encountered. The foliage possesses a slight gloss. The mint fragrance of the leaves commonly is very strong.

The new cultivar can be readily distinguished from its ancestors through an inspection of the blossom coloration. More specifically, the 'Mahogany' female parent forms bright red blossoms, and the 'Marshall's Delight' cultivar forms dissimilar pink blossoms.

The new cultivar of the present invention well meets the needs of the horticultural industry and suitable for growing in the landscape as a specimen or in a mass planting.

The new cultivar has been asexually reproduced by the rooting of cuttings at Morden, Manitoba, Canada, and at St. Paul, Minn., U.S.A. The combination of characteristics exhibited by the new plant has been found to be stable and is reliably transmitted to succeeding generations following such asexual reproduction. Accordingly, the new cultivar reproduces true to type by such asexual propagation.

The new cultivar of the present invention has been named 'Coral Reef'.

BRIEF DESCRIPTION OF THE PHOTOGRAPHS

The accompanying photographs show, as nearly true as it is reasonably possible to make the same in color illustrations of this character, typical specimens of the new cultivar. The *Monarda* plants were reproduced by the rooting of cuttings, were approximately two and three years of age, and were grown outdoors during the 2003 season at St. Paul, Minn., U.S.A.

FIG. 1 illustrates at the center a mature plant of the 'Coral Reef' cultivar which displays the customary upright and mounded growth habit.

Figure 2:
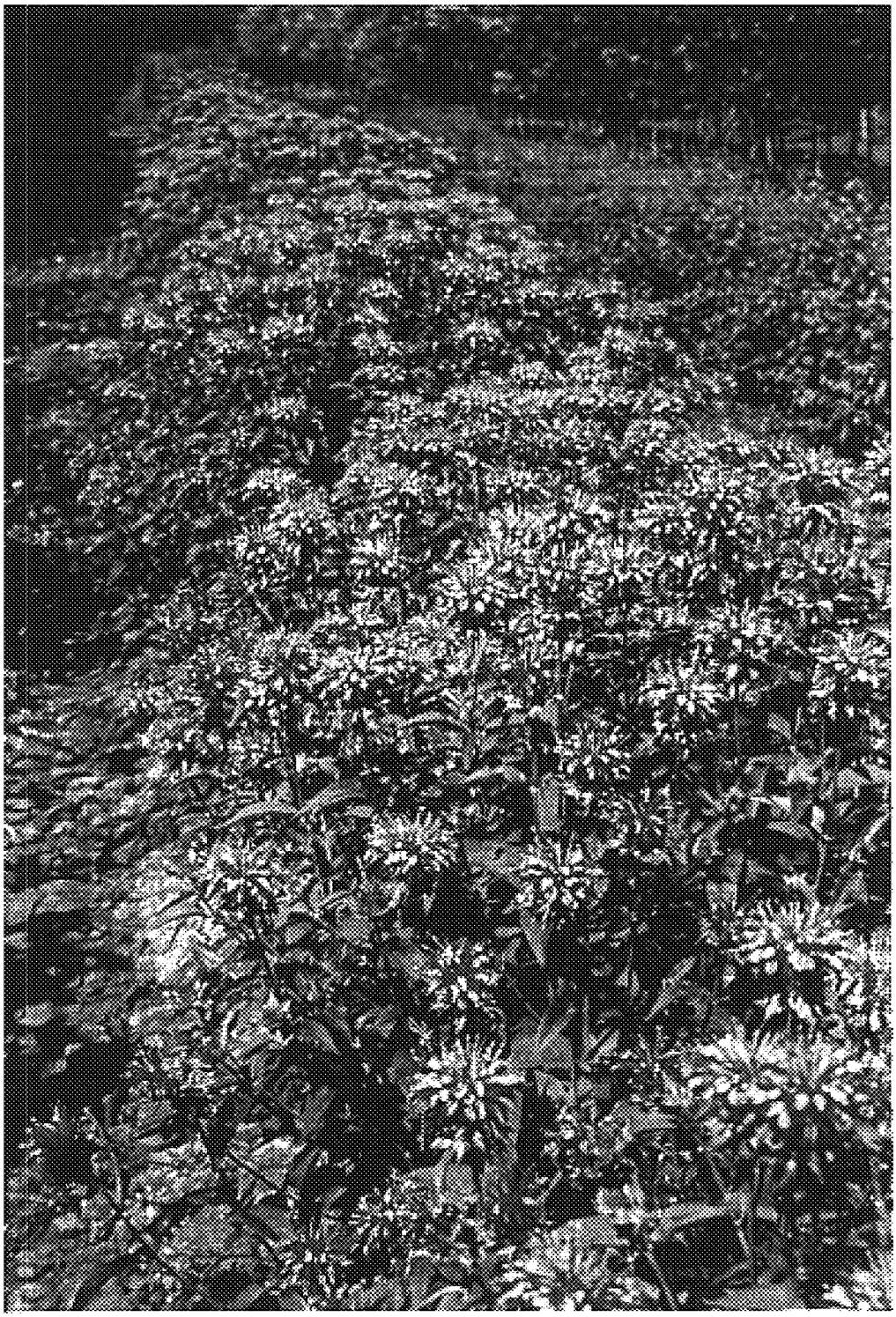

FIG. 2 illusrates a nursery row of plants of the 'Coral Reef' cultivar wherein the bright coral pink blossoms are shown in greater detail in the foreground.

DETAILED DESCRIPTION

The described plants had been asexually propagated by the rooting of cuttings, were approximately one and two years of age, and were observed during June and August, 2003 while growing outdoors at St. Paul, Minn., U.S.A. The chart used in the identification of color is The R.H.S. Colour Chart of The Royal Horticultural Society, London, England. Reference to common color terms is to be accorded ordinary dictionary significance.

Botanical classification: *Monarda didyma* cv. 'Coral Reef'.

Plant:

*Growth habit*.—Upright and mounded in configuration.

*Size*.—Commonly approximately 90 cm to 1.25 m (approximately 3 to 4 feet) in height on average when mature, and approximately 60 cm to 80 cm (approximately 2 to 2.5 ft) in width on average when mature.

*Lateral branches*.—Number: Commonly approximately six on average on a central branch length of 18 inches. Length: Commonly approximately 13 inches on average at the middle, and approximately 6 inches on average at the top of the plant. Diameter: Commonly approximately 2.5 cm on average. Internode Length: Commonly approximately 4.8 cm on average. Color: Between Yellow-Green Group 146A and 146B with some streaking of Greyed-Purple Group 185A on the lateral edges. Texture: Pubescent.

Foliage:

*Configuration*.—Ovate to ovate-lanceolate.

*Arrangement*.—Opposite.

*Apex*.—Acuminate.

*Base*.—Rounded to cordate.

*Size*.—Leaves commonly measure approximately 7 cm in length on average and approximately 3.25 cm in width on average. The leaf size is similar to that of the 'Marshall's Delight' cultivar.

*Margins*.—Serrulate.

*General appearance*.—Medium density, dark green with a slight gloss. The foliage possesses less glossiness than the 'Petite Wonder' cultivar (U.S. Plant Pat. No. 13,149).

*Color*.—Young Foliage: Yellow-Green Group 144A on the upper and under surfaces. Adult Foliage: Commonly between Yellow-Green Group 147A and 147B on the upper surface and between Yellow-Green Group 146B and 147B on the under surface.

*Stems*.—Four-sided in structure, and the coloration is Yellow-Green Group 144B and 144C with highlights of Red-Purple Group 59A and 59B on young stems and between Yellow-Green Group 144B and 144C with highights of Greyed-Orange Group 177A on adult wood.

*Petiole*.—Length: Approximately 1.0 cm on average. Diameter: Approximately 2.0 cm on average. Color: Yellow-Green Group 145B on the upper side with Greyed-Purple Group 185A on the lateral edges, and Yellow-Green Group 145A on the under side. Texture: Pubescent on the upper side.

Inflorescence:

*Natural flowering season*.—Commonly heavy blooming from June through August. Such bloom period can be extended by deadheading accompanied by a lesser bloom density.

*Buds*.—Shape: As an elongated tube. Length: Commonly approximately 2.3 cm on average. Diameter: Commonly approximately 3 mm on average. Color: Red-Purple Group 61B.

*Verticillasters*.—Bearing: Approximately 51 substantially tubular florets on average are terminally present in single or double whorl on a mature plant when blooming. Diameter: Approximately 7.5 cm on average. Height: Approximately 4.6 cm on average.

*Florets*.—Shape: Each is substantially tubular and includes a keel or upper lobe and a lower lobe, the keel or upper lobe is rounded, and the lower lobe is truncate with a rectangular tongue-like extension. Depth: Commonly approximately 3.2 cm on average.

*Color*.—When opening begins the upper surface is Red Group 54A and the under surface is Red-Purple Group 58A, and when blooming the upper surface is Red-Purple Group 58B and the under surface is Red Group 55B.

*Stamen*.—Number: Two. Filament Length: Approximately 2.25 cm on average. Filament Color: Yellow Group 4D. Anthers: Approximately 4.5 mm in length, approximately 1.8 mm in width, and Greyed-Red Group 180A with some Orange-White Group 159A on the upper side. Pollen: Sparse and near Yellow-Orange Group 15B in coloration.

*Pistil*.—Number: One. Style Length: Approximately 2.5 cm on average. Style Color: Near Red Group 56C and near White Group 155A on the exserter portion outside the florets. Stigma Size: Approximately 4.1 mm in length on average, and appoximately 1 mm in width on average. Ovary: Tiny with one ovule.

*Seeds*.—Number: Typically one per floret. Shape: Oval to rice-shaped. Length: Approximately 1.8 mm on average. Width: Approximately 1 mm on average. Color: Grey-Brown Group 199A with some highlights of Brown Group 200D.

*Flower longevity*.—Approximately 5 to 7 days when on the plant depending upon environmental conditions.

*Fragrance*.—The flowers, stems, and foliage display a strong minty fragrance.

*Sepals*.—Number: Typically 12 per verticillaster. Shape: Generally lanceolate. Length: Approximately 2.2 cm on average. Width: Approximately 3.4 mm on average. Color: On the upper surface Yellow-Green Group 147D with some highlights of Yellow-Green Group 147C and streaking of Greyed-Purple Groups 186A and 186B, and on the under surface Yellow-Green Groups 148C with highlights of Greyed-Purple Group 186A that is present primarily at the margin and apex.

*Bracts*.—Number: Typically 9 per verticillaster. Shape: Ovate to lanceolate. Length: Commonly approximately 3.2 cm on average. Width: Commonly approximately 1.5 cm on average. Color: On the upper surface Yellow-Green Group 147C with highlights of Yellow-Green Group 148D and Greyed-Purple Group 185D, and on the under surface Yellow-Green Group 146C with highlights of Greyed-Purple Group 185C.

*Peduncle*.—Length: Commonly approximately 8 cm on average. Diameter: Commonly approximately 5 mm on average. Color: Yellow-Green Group 147C with highights of Greyed-Purple Group 186A.

Development:

*Vegetation*. —Medium density.

*Culture*.—Performs well in full sun.

*Disease resistance*.—Good resistance to Powdery Mildew has been observed.

*Insect resistance*.—No major insect problems have been encountered.

*Hardiness*.—Plants are hardy in U.S.D.A. Hardiness Zone Nos. 3 to 8.

*Propagation*.—Plants of the new variety can be readily propagated by the use of rhizome and softwood stem cuttings.

*Usage*.—The new variety can be used in traditional formal beds to provide attractive blooms. Large mass plantings are possible. Plants can be used as specimens or as borders defining sections of beds or boundaries. The dark green foliage contasts well with the bright coral pink flowers.

I claim:

1. A new and distinct *Moranda* plant having the following combinations of characteristics:

(a) forms attractive bright coral pink blossoms, (b) forms attractive dark green leaves that display a strong minty fragrance, (c) displays an upright mounded growth habit and commonly assumes a mature height of approximately three to four feet, (d) grows well in U.S.D.A. Hardiness Zone Nos. 3 to 8, (e) displays good resistance to Powdery Mildew, and (f) is well suited for growing as attractive ornamentation in the landscape;

substantially as illustrated and described.

* * * * *